United States Patent [19]

Higaki

[11] Patent Number: Plant 6,234

[45] Date of Patent: Jul. 26, 1988

[54] CACTACEAE PLANT NAMED RUDOLPH

[75] Inventor: Harry Higaki, San Mateo, Calif.

[73] Assignee: Bay City Flower, Co., Half Moon Bay, Calif.

[21] Appl. No.: 851,789

[22] Filed: Apr. 14, 1986

[51] Int. Cl. ..... A01H 5/00

[52] U.S. Cl. ..... Plt./88

[58] Field of Search ..... Plt./88

*Primary Examiner*—Robert E. Bagwill

*Attorney, Agent, or Firm*—James R. Cypher

EXEMPLARY CLAIM

A new and distinct plant variety of the Cactaceae family obtained through cross-pollination of *Schlumbergera truncata* "Christmas Charm" and *Schlumbergera truncata* "Maria", distinguished from its parents and other known related varieties by a growth habit which combines a "reddish" colored bloom, a more vigorous growth rate than both parents, breaking propensity comparable to its paternal parent and better than its maternal parent, vigorous free budding and free flowering comparable to its paternal parent and better than its maternal parent, an upright and dense appearance and considerable resistance to nutrient deficiencies and fungus type diseases.

1 Drawing Sheet

BACKGROUND OF THE INVENTION

The invention relates to a new and distinct plant variety of the Cactaceae family which has been named *Schlumbergera truncata* "Rudolph" by the inventor.

Certain plant varieties of the Cactaceae family, which are among those of the truncata species of the Schlumbergera genus, tend to bloom in the months of November and December in the Northern Hemisphere. Because of their blooming time they appear in the market primarily during the Thanksgiving and Christmas seasons, and hence the common name Christmas Cactus. During the Christmas season, a "reddish" colored bloom is often very desirable. There are many "reddish" colored varieties available on the market, but none of the varieties combine the characteristics of having a fast growth rate, good breaking, and free budding and flowering. The "reddish" varieties that are available are either slow growing with good breaking, and free budding and flowering characteristics, or fast growing with poor breaking, and low budding and flowering characteristics.

The main objective of the invention has been to develop a variety of the Cactaceae family with a "reddish" colored bloom that has a fast growth rate, a vigorous breaking propensity and is free budding and free flowering. Another objective has been to develop a variety that also has an upright and dense appearance, and has suitable resistance to nutrient deficiencies and fungus type diseases.

The objectives of the invention have been obtained by the development of the new variety. The new variety was developed in a nursery located in Half Moon Bay, Calif., as a hybrid obtained through the cross-pollination of *Schlumbergera truncata* "Christmas Charm" and *Schlumbergera truncata* "Maria". "Christmas Charm" being the paternal parent and "Maria" the maternal parent. The seeds taken from the fertilized seed pod were cultivated at the Half Moon Bay nursery and, after observation of the seedlings, the hybridized plant of the new variety was selected and asexually reproduced by the inventor at the nursery by the propagation of stem cuttings taken from the original hybrid plant.

Through successive propagations, it has been recognized that specimens of the new variety resemble the parent varieties, but are distinguishable from the parents and other related varieties known to me, by a growth habit which is clearly visible in the specimens propagated and grown under nursery conditions at the Half Moon Bay location, as combining the following characteristics:

1. A "reddish" colored bloom.
2. A faster growth rate than both parents.
3. Breaking propensity comparable to the paternal parent and better than the maternal parent.
4. A vigorous free budding and flowering habit comparable to the paternal parent and better than the maternal parent.
5. An upright and dense appearance.
6. Considerable resistance to nutrient deficiencies and fungas type diseases.

BRIEF DESCRIPTION OF THE DRAWING

The accompanying drawings serve, by color photographic means, to illustrate the new plant variety and wherein.

DETAILED DESCRIPTION OF THE DRAWING

Figure 1:
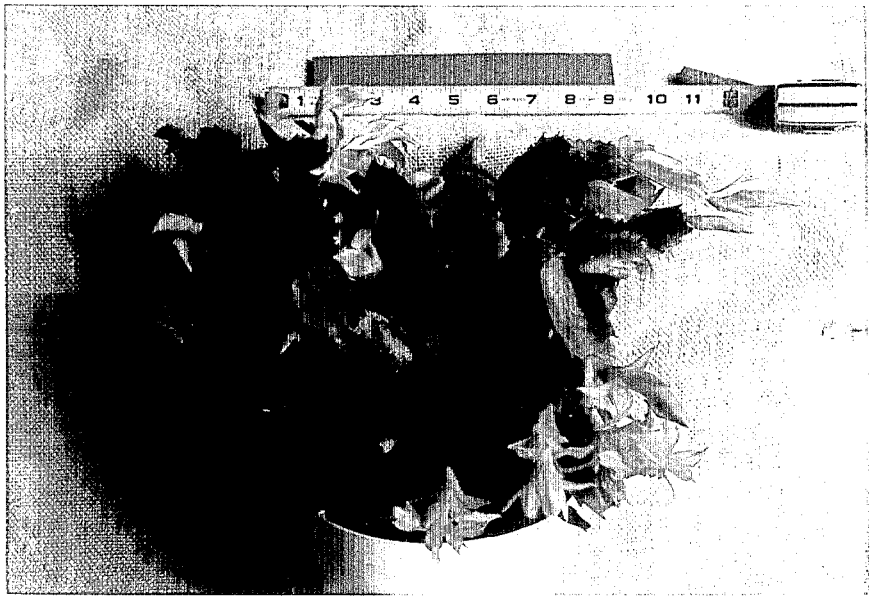
FIG. 1 is a color photograph of a potted plant of the new variety illustrating the overall appearance and form of the plant.
Figure 2:
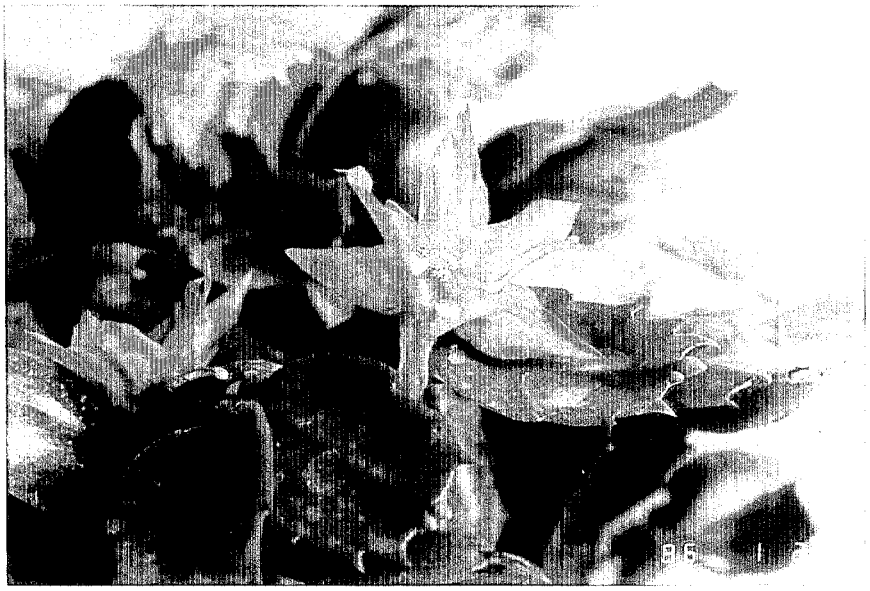
FIG. 2 is a color photograph showing a fully opened bloom of the new variety together with buds of the new variety.

The following is a detailed description of the new variety with colors and hues being named in accord with the Horticultural Colour Chart issued by the British Colour Council in collaboration with The Royal Horticultural Society (two volume set issued separately in 1938 and 1942). The following description is based on observations of well fertilized plants of 16–18 months of age from initial propagation which were grown under 50–70% shaded polyhouse nursery conditions in Half Moon Bay, Calif., where temperatures average from 55° to 65° F. during the summer months, and from 45° to 55° F. during the winter months.

DETAILED PLANT DESCRIPTION

I. Name: *Schlumbergera truncata.*

II. Parentage:

*Maternal.*—*Schlumbergera truncata* "Maria" (*Zygocactus truncatus* "Maria").

*Paternal.*—*Schlumbergera truncata* "Christmas Charm" (*Zygocactus truncatus* "Christmas Charm").

III. Classification:

*Botanic.*—(Britton and Rose, The Cactaceae, Constable and Co., Ltd., London, 1937, Vol. IV). (Bailey and Bailey and the staff of the Bailey Hortorium, Hortus Third, 1976).

| | |
|---|---|
| (1) Family: | Cactaceae |
| (2) Tribe: | Cereeae |
| (3) Sub-tribe: | Epiphyllanae |
| (4) Genus: | Schlumbergera |
| (5) Species: | Truncata (Haw.) Moran |

*Commercial.*—Thanksgiving cactus.

IV. Form: Terrestrial, shade-loving, succulent, leafless plant with jointed and branched stems.

V. Stems:

A. *General.*—Irregular with usually mono-chotomous to di-chotomous branching of mostly upright, adventitiously rootable, irregularly strongly revolute to flattened phylloclades that have a prominent midrib and prominently toothed lateral wings.

B. *Phylloclades.*—(1) General: Elongated with strong revolute character of the youngest phylloclades with the overall orientation that of a convex surface for one side of a phylloclade and a corresponding concave surface of the opposing side of the phylloclade, the phylloclades becoming mostly flattened with age. Phylloclades with transversely elongate, areole bearing truncated apex, with inwardly tapering basal wing margins that merge through a broad, usually pointed basal juncture with the phylloclade below and with an axiallary areole associated with each tooth. (2) Midrib: General — Extends longitudinally of phylloclade and continuously through joints with laterally tapering cortex at wing insertions. Pith surrounding vascular bundles that branch and provide lateral extensions of the vascular system to marginal teeth. Texture: Smooth, waxy epidermis with wax in small embedded scales and becoming corky in basal stem areas with age. Size (18 mos) — Length: Usually between 47 and 57 mm with the average for respective plant specimens being usually between 50 and 54 mm. Thickness: usually between 1.5 and 4.5 mm with the average for respective plant specimens being between 2.2 and 3.7 mm. Color (at maturity): commonly spinach green (0960/2) to (0960/3). (3) Wings. — general shape: Generally strongly revolute when young becoming flattened with age from midrib cortex to tooth insertions with thinning taper toward margins. Margins: toothed. Texture: succulent to slightly coriaceous with smooth, waxy epidermis having wax arranged in small embedded scales and becoming corky in basal plant areas with age. Size (18 mo). — Center thickness: usually between 0.8 and 1.8 mm. Width (measured from phylloclade axis to most offset lateral areole): usually between 12.5 and 21.2 mm. Color (at maturity): commonly spinach green (0960) to (0960/1). (4) Teeth. — General: Generally flattened and tapering along margins from wing insertions to an apex having a hyaline, pointed spine with random bending. Adaxial marginal shape: generally straight for larger teeth to distinctly concave for smaller teeth. Adaxial marginal shape: irregular, varying from being distinctly convex to generally straight or with the distal terminus being slightly convex. Orientation: usually projects distally of the phylloclade base in an alternate arrangement. Margins: entire. Texture: succulent to coriaceous with smooth, waxy epidermis having wax in small embedded scales and becoming corky in basal plant areas with age. Number: usually 6 to 8 per phylloclade. Size (18 mo ). — Center thickness: usually between 0.5 and 1.2 mm. Areole to apex dimension (adaxial marginal side): usually between 0.2 and 5.2 mm for teeth located distally of basal teeth. Color (at maturity): commonly Scheeles green (860/3). (5) Areoles: terminal areole — Large elongated oval-shape with several acicular bristles and a dense mate of multi-cellular hairs and several buds that may mature into either new phylloclades of flowers. The opposing ends of the areoles are located adjacent to subsidiary areoles which are in turn located at the axils of teeth that are located at the distal end of the phylloclade. Axillary areoles: acicular bristles without glochidia but having numerous short colorless or light brown, multicellular hairs.

VI. Buds: Unarmored, ovid and chlorophyllous when first emerging.

VII. Flowers:

A. *General.*—Sessile, zygomorphic, usually in pairs, occasionally solitary or in clusters ranging up to four, terminal, perfect, epigynous with double hypanthium and tepals having aspiral emergence as a perianth provided with a sepaloid series of free tepals, a tube laminating series of tepals, and a tube forming series of united tepals.

B. *Sepaloid series.*—(1) General: free tepals inserted on top of the ovary. (2) Shape: deltoid in outer members of the whorl and with the inner members being irregular in shape varying from elliptic to slightly oblanceolate, tips of tepals are acute in outer members of the whorl and acuminate for inner member of the whorl. Margins are entire or with sparse irregular teeth for the apical portion of the inner members of the whorl. (3) Texture: succulent and glabrous outer whorl members and grading inwardly in the whorl to thin blades with fleshy basal areas. (4) Number: usually 9 or 10 (5) Size (at full bloom): base-tip dimension — usually less than 30 mm, range for longest tepal of the sepaloid series between 25 and 30 mm. Maximum width dimension — less than 15 mm, range of maximum between 11 and 15 mm. (6) Color: outer whorl members — Varies with position of tepal within the whorl. Smallest outer whorl members with a uniform field that in color is of a violet-red hue. The larger outer whorl members are characterized by violet-red basal areas merging distally with red hued marginal and apical zones. The outer whorl members are basally magenta to magenta rose, (27/2) to (027/2), with the marginal and distal zones being spiraea red (025/2) with the transition zone of color fusion between the basal and marginal areas being rose bengal to spiraea red, (25/3 to 025/3). Inner whorl members have basal areas dominated by magenta (27/3) intensifying to magenta (27/2) immediately distal to the basal area. Marginal areas are dominated by rose bengal (25/1) (25/2) intergrading to geranium lake (20/1) (20/2) as the marginal and the area immediately distal to the basal area merge. (7) Orientation at full bloom: generally acute to slightly reflexed.

C. *Tube laminating series.*—(1) General: tepals inserted on ovary and basally united below the throat as outer laminations on the perianth tube and with progressively greater amounts of basal fusion inwardly in the whorl. (2) Shape: grading inwardly in whorl with progressively longer base-tip dimensions and with oblanceolate to spatulate tepals and with the free portion of the blade being lanceolate to slightly oblanceolate, tip narrow to broadly acute generally with a short apiculate ultimate apex. Margins mostly entire at base with very small, sparse and irregular teeth on the margin from near the middle of the tepal to the apex. (3) Texture: succulent and fleshy basal area, thin and soft blades. (4) Number: usually 4 to 6. Size (at full bloom): Base-tip usually between 26 and 56 mm. Maximum width dimensions: usually between 13 and 17 mm. (5) Color: tepals with magenta basal areas (27/3) distally becoming more intensely colored (27/2). The marginal area of the blades of the tube laminating series is rose bengal (25/1) (25/2), intergrading to geranium lake (20/1) (20/2) as the marginal and distal basal areas merge.

D. *Tube forming series.*—(1) General: tepals basally united to form perianth tube that is inserted on ovary and equipped with a vestigial carina at the throat. (2) Shape: perianth tube — Enlongatd and ellipsoidal in cross-section. Blades elliptic to slightly oblanceolate, tips acute to slightly acuminate. Margins basally entire, apically with small irregular teeth. Carina: vestigial at throat of perianth tube. (3) Texture: perianth tube — thick, succulent, slightly ribbed at point of lateral fusion of tepals. Blades: proximally fleshy, distally thin and solf. Carina: fleshy. (4) Blade number: usually 8. (5) Size (at full bloom): perianth tube — base to keel length. Usually between 32 and 36 mm along axis of tube with average length difference between measurements along dorsal and ventral sides for respective specimens usually between 2.0 and 4.5 mm. Internal major axis (at throat): usually between 8 and 11 mm when measured perpendicular to axis of perianth tube. Internal minor axis (at throat): usually between 4 and 8 mm when measured perpendicular to axis of perianth tube. Blades — length (keel to tip): usually between 25 and 33 mm. width (maximum): usually between 12 and 15 mm. (6) Color (at full bloom): perianth tube — usually translucent white with lines marking lateral fusion of tepals light magenta (27/3). Blades — Tepal blades with marginal blade areas which in color are dominated by rose bengal (red) to geranium lake (red) that merges with a violet-red (magenta) for the basal blade area that extends distally of the throat. The basal area magenta (27/3) distally becomes geranium lake (20/1) and merges with the marginal area rose bengal (25/1). Carina: characterized by an intense fuchsia purple (28/1) to strong peony purple (729/2). Orientation at full bloom: reflexed.

E. *Androecium (stamens).*—(1) General: numerous excerted and diadelphous stamens with one group having filaments basally fused to the perianth tube and the other group having filaments basally united to form a nectary housing, thin annulus around the style and which is provided with a thin, slightly deflexed, irregularly toothed margin at the throat of the annulus. (2) Stamen number: tube attached group — usually between 18 and 22. Basally united group — usually between 18 and 22. (3) Filament general: translucent white and glabrous with anther connective. Shape: long, slender, gradually tapering from base to anther connective. Texture: glabrous and smooth. Color: translucent white. Size (at full bloom) length: tube attached group — usually between 37 and 45 mm. Basally united group: usually between 39 and 45 mm. Diameter: usually between 0.2 and 0.3 mm intermediate the opposing ends. (4) Anthers generally: adnate with four longitudinally dehiscent pollen sacs. Shape: elongated. Texture: waxy. Color (post dehiscence, pollen color): usually greenish-yellow, uranium green (63/2).

F. *Gynoecium (pistil).*—(1) General: compound, parietal placentation with a united style surrounded by an annular diffuse nectary at its insertion. (2) Style general: stout and inserted in ovary. Shape: elongated cylindrical and generally tapering. Texture: fleshy and glabrous. Color: proximal end is pure magenta (27) gradually changing to fuchsia purple (28) at the distal end of the style. Size (at full bloom): Length: usually about 56 mm. Diameter: usually between 0.6 and 0.8 mm intermediate the opposing ends. (3) Stigma — General: exserted and erect with usually 6 or 7 inner marginally adhering lobes. Shape: elongated and tapering toward lobe tips and having relatively blunt apices. Texture: fleshy with short glutinous hairs. Color: area proximal to point of attachment of stigma to style persian rose (628/1) distally decreasing in intensity to (628/2) and (628/3) at the tips of the stigma lobes. Size (lobe length at full bloom): usually between 2.8 and 4.2 mm. (4) Ovary General: epigynous with thin epidermis and distally located concavity and with single cavity usually having 6 or 7 carpels with numerous ovules. Shape: terete to ovoid, broadening from insertion to floral end. Texture: succulent and glabrous with thin epidermis. Color: mostly translucent white or very light green-yellow or chartreuse (663/3) with portion immediately distal to point of attachment to phylloclade rhodamine pink (527/3) and portion immediately bordering attachment of tepals magenta (27/3). Size (at full bloom) — Length (insertion to concavity base): usually between 7 and 10 mm. Major axis (distal end of concavity): usually between 7 and 8 mm. Minor axis (distal end of concavity): usually between 6 and 8 mm.

The following is a general description of a flower of the new plant variety grown at Half Moon Bay, Calif., under greenhouse nursery conditions.

Bloom life: 8 Days.

Sepaloid series of tepals:

(1) *Number.*—10.

(2) *Size (at full bloom).*—Maximum base-tip dimension: 26 mm. Minimum base-tip dimension: 3 mm. Maximum width dimension: 12 mm.

(3) *Color.*—Most outer whorl basally magenta (27/2) to magenta rose (027/2), marginal and distal areas spiraea red (025/2) with transition zone of rose bengal (25/3) to spiraea red (025/3) between basal and marginal areas. Inner whorl members basally magenta (27/3) becoming more intensely colored (27/2) distally, marginal zones rose bengal (25/1) (252) with transition zone of geranium lake (20/1 (20/2).

Tube laminating series:

(1) *Number.*—6.

(2) *Size (at full bloom).*—Maximum base-tip dimension: 56 mm. Minimum base-tip dimension: 26 mm. Maximum width dimension: 13 mm. Minimum width dimension: 10 mm.

(3) *Color.*—Basally magenta (27/3) (27/2), marginal blade area rose bengal (25/1) (25/2).

Tube forming series:

(1) *Number.*—8.

(2) *Size (at full bloom).*—Perianth tube: Base to throat length 34 mm. Interior major axis (at throat): 10 mm. Interior minor axis (at throat): 6 mm. Blades: maximum length (throat to tip) 28 mm. Minimum length (throat to tip): 26 mm. Maximum width: 14 mm. Minimum width: 12 mm.

(3) *Color.*—Perianth tube: translucent white with the lines of lateral fusion of tepals light magenta (27/3). Blades: basally magenta (27/3) distally becoming genanium lake (20/1), marginal areas are rose bengal (25/1). Carina: Fuchsia purple (28/1) to peony purple (729/2).

Androecium:

(1) *Stamen number.*—Tube attached group: 90. Basally united group: 19.

(2) *Filaments.*—Color: translucent white. Size (at full bloom): Length — tube attached group: 43 mm (avg.). Basally united group: 41.5 mm (avg.). Diamter: 0.25 mm (avg.).

(3) *Anthers.*—Color (post dehiscense): Uranium green (63/2).

Gynoecium:

(1) *Style.*—Color: Proximal end pure magenta (27), distally becoming fuchsia purple (28). Size (at full bloom): Length — 56 mm. Diameter — 0.7 mm intermediate the two opposing ends.

(2) *Stigma.*—Color: Proximally persian rose (628/1) decreasing in intensity distally to (628/2) or (628/3). Size (lobe length.) 3.5 mm (avg.).

(3) *Ovary.*—Color: Translucent white to very light green-yellow or chartreuse green (663/3) with zone immediately distal to attachment with phylloclade rhodamine pink (527/3) and the portion immediately bordering attachment of tepals magenta (27/3). Length (insertion to concavity base) — 10 mm. Major axis (distal end of concavity) — 8 mm. Minor axis (distal end of concavity) — 7 mm.

The following is a general description of a specimen of the new plant variety that was grown from the propagation of a single phylloclade in a nursery at Half Moon Bay, Calif.

Age from initial propagation: 18 months.

Branches from propagated cutting: 7.

Total number of phylloclades grown from cutting: 77.

General:

| Branch No. | No. of Phylloclades | Max. Length | No. of Tips |
|---|---|---|---|
| 1 | 28 | 219 mm | 11 |
| 2 | 24 | 197 mm | 11 |
| 3 | 14 | 223 mm | 5 |
| 4 | 6 | 175 mm | 2 |
| 5 | 3 | 76 mm | 2 |
| 6 | 1 | 29 mm | 1 |
| 7 | 1 | 19 mm | 1 |

Midribs:

| Branch No. | Length (avg.) | Thickness (avg.) |
|---|---|---|
| 1 | 47.9 mm | 3.3 mm |
| 2 | 42.8 mm | 2.9 mm |
| 3 | 49.8 mm | 3.4 mm |
| 4 | 45.8 mm | 2.2 mm |
| 5 | 39.7 mm | 2.0 mm |
| 6 | 32.0 mm | 1.2 mm |
| 7 | 19.0 mm | 1.7 mm |

Wings:

| Branch No. | Center Thickness (avg.) | Max. Width (avg.) |
|---|---|---|
| 1 | 1.4 mm | 35.2 mm |
| 2 | 1.2 mm | 32.4 mm |
| 3 | 1.1 mm | 30.2 mm |
| 4 | 1.0 mm | 31.3 mm |
| 5 | 0.9 mm | 25.3 mm |
| 6 | 0.8 mm | 10.0 mm |
| 7 | 1.2 mm | 8.0 mm |

Teeth:

| Branch No. | No./Phylloclade (avg.) | Center Thickness (avg.) | Areole to Apex Dimension (avg.) |
|---|---|---|---|
| 1 | 6.5 | 0.7 mm | 2.7 mm |
| 2 | 7.0 | 0.6 mm | 3.2 mm |
| 3 | 6.4 | 0.6 mm | 3.7 mm |
| 4 | 6.3 | 0.5 mm | 3.7 mm |
| 5 | 6.0 | 0.5 mm | 2.1 mm |
| 6 | 6.0 | 0.6 mm | 0.7 mm |
| 7 | 5.0 | 0.7 mm | 0.5 mm |

Phylloclade color: Spinach green (0960) (0960/1) to Scheeles green (860/3).

I claim:

1. The new and distinct hybrid plant variety of the Cactaceae family substantially as herein shown and described.

* * * * *